United States Patent [19]

Abuto et al.

[11] Patent Number: 5,964,743

[45] Date of Patent: *Oct. 12, 1999

[54] ELASTIC ABSORBENT MATERIAL FOR PERSONAL CARE PRODUCTS

[75] Inventors: Frank Paul Abuto; Penny Atieno Abuto, both of Duluth; Stanley Michael Gryskiewicz, Woodstock, all of Ga.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/806,731

[22] Filed: Feb. 27, 1997

[51] Int. Cl.$^6$ .................................................. A61F 13/15
[52] U.S. Cl. ..................... 604/385.1; 604/368; 604/385.2
[58] Field of Search ..................... 604/378, 380, 604/385.1, 358, 368

[56] References Cited

U.S. PATENT DOCUMENTS

| | | | |
|---|---|---|---|
| 1,003,487 | 9/1911 | Miller-Jones | 604/358 |
| 1,863,333 | 6/1932 | Heitmeyer | 604/380 |
| 2,896,618 | 7/1959 | Schaefer | 604/378 |
| 3,338,992 | 8/1967 | Kinney . | |
| 3,341,394 | 9/1967 | Kinney . | |
| 3,502,763 | 3/1970 | Hartmann . | |
| 3,542,615 | 11/1970 | Dobo et al. . | |
| 3,692,618 | 9/1972 | Dorschner et al. . | |
| 3,802,817 | 4/1974 | Matsuki et al. . | |
| 3,849,241 | 11/1974 | Butin et al. . | |
| 4,027,672 | 6/1977 | Karami | 604/385.1 |
| 4,100,324 | 7/1978 | Anderson et al. . | |
| 4,323,534 | 4/1982 | DesMarais . | |
| 4,340,563 | 7/1982 | Appel et al. . | |
| 4,374,888 | 2/1983 | Bornslaeger . | |
| 4,542,199 | 9/1985 | Kaminsky et al. . | |
| 4,663,220 | 5/1987 | Wisneski et al. . | |
| 4,676,786 | 6/1987 | Nishino | 604/385.1 |
| 4,707,398 | 11/1987 | Boggs . | |
| 4,724,184 | 2/1988 | Killian et al. . | |
| 4,741,949 | 5/1988 | Morman et al. . | |
| 4,753,645 | 6/1988 | Johnson | 604/385.1 |
| 4,803,117 | 2/1989 | Daponte . | |
| 4,818,464 | 4/1989 | Lau . | |
| 4,820,572 | 4/1989 | Killian et al. . | |
| 4,834,738 | 5/1989 | Kielpikowski et al. . | |
| 4,923,742 | 5/1990 | Killian et al. . | |
| 5,064,802 | 11/1991 | Stevens et al. . | |
| 5,093,422 | 3/1992 | Himes . | |
| 5,108,827 | 4/1992 | Gessner . | |
| 5,151,091 | 9/1992 | Glaug et al. | 604/385.1 |
| 5,189,192 | 2/1993 | LaPointe et al. . | |
| 5,204,429 | 4/1993 | Kaminsky et al. . | |
| 5,272,236 | 12/1993 | Lai et al. . | |
| 5,275,591 | 1/1994 | Mavinkurve | 604/385.1 |
| 5,277,976 | 1/1994 | Hogle et al. . | |
| 5,278,272 | 1/1994 | Lai et al. . | |
| 5,302,454 | 4/1994 | Cecchin et al. . | |

(List continued on next page.)

FOREIGN PATENT DOCUMENTS

| | | |
|---|---|---|
| 556749A1 | 8/1993 | European Pat. Off. . |
| 2284831 | 6/1995 | United Kingdom . |
| 95/21596 | 8/1995 | WIPO . |
| 96/19173 | 6/1996 | WIPO . |

OTHER PUBLICATIONS

*Science,* vol. 267 (Jan. 13, 1995) at p. 191, article entitled "Oscillating Catalysts: A New Twist for Plastics" by K. B. Wagener.

*Primary Examiner*—John G. Weiss
*Assistant Examiner*—Dennis Ruhl
*Attorney, Agent, or Firm*—James B. Robinson

[57] ABSTRACT

There is provided a stretchable absorbent material for personal care products which has a liquid permeable top sheet, a bottom sheet, and beams of an absorbent composition between the top and bottom sheets whereby the beams are spaced apart by bond rows therebetween. The stretchable absorbent material provides a more conformable product and can aid in moving liquid away from the target zone, and in air circulation within the product.

11 Claims, 2 Drawing Sheets

U.S. PATENT DOCUMENTS

| | | |
|---|---|---|
| 5,304,599 | 4/1994 | Himes . |
| 5,332,613 | 7/1994 | Taylor et al. . |
| 5,349,100 | 9/1994 | Mintz . |
| 5,352,749 | 10/1994 | DeChellis et al. . |
| 5,368,927 | 11/1994 | Lesca et al. . |
| 5,374,696 | 12/1994 | Rosen et al. . |
| 5,382,400 | 1/1995 | Pike et al. . |
| 5,382,467 | 1/1995 | Widlund et al. . |
| 5,399,175 | 3/1995 | Glaug et al. ............... 604/385.1 |
| 5,451,219 | 9/1995 | Suzuki et al. ............... 604/358 |
| 5,614,283 | 3/1997 | Potnis et al. ............... 604/385.1 |
| 5,662,634 | 9/1997 | Yamamoto et al. ............... 604/380 |

ELASTIC ABSORBENT MATERIAL FOR PERSONAL CARE PRODUCTS

BACKGROUND OF THE INVENTION

Absorbent systems for personal care products usually store substantially all liquid insults in the crotch region and are not stretchable and have no retraction towards the original shape. This results in the crotch region being heavily loaded with liquid by the first insult and can result in insufficient capacity for a second, third or later insult. This crotch area loading can cause the product to sag away from the wearer, causing discomfort for the wearer and creating the possibility of leakage. The lack of stretchability and retraction can cause lack of conformity to the body of the wearer and so allow leakage with the resultant staining of garments, bedding etc.

An absorbent which stretched to conform to the body despite movement of the wearer and which could help to move liquid away from the target area, would be preferable to the non-stretchable, crotch-area storage design.

It an object of this invention, therefore, to provide a stretchable absorbent for personal care products. It is a further object of this invention to provide a stretchable absorbent which can provide a way for liquid to travel to areas away from the target area. Other important advantages to this stretchable absorbent system will be elaborated upon below.

SUMMARY OF THE INVENTION

The objects of this invention are achieved by an absorbent material which is stretchable and includes valleys which may direct liquid in various directions. The absorbent material for personal care products has a liquid permeable top sheet, a bottom sheet, and beams of an absorbent composition between the top and bottom sheets whereby the beams are spaced apart by bond rows therebetween.

DEFINITIONS

Figure 1:
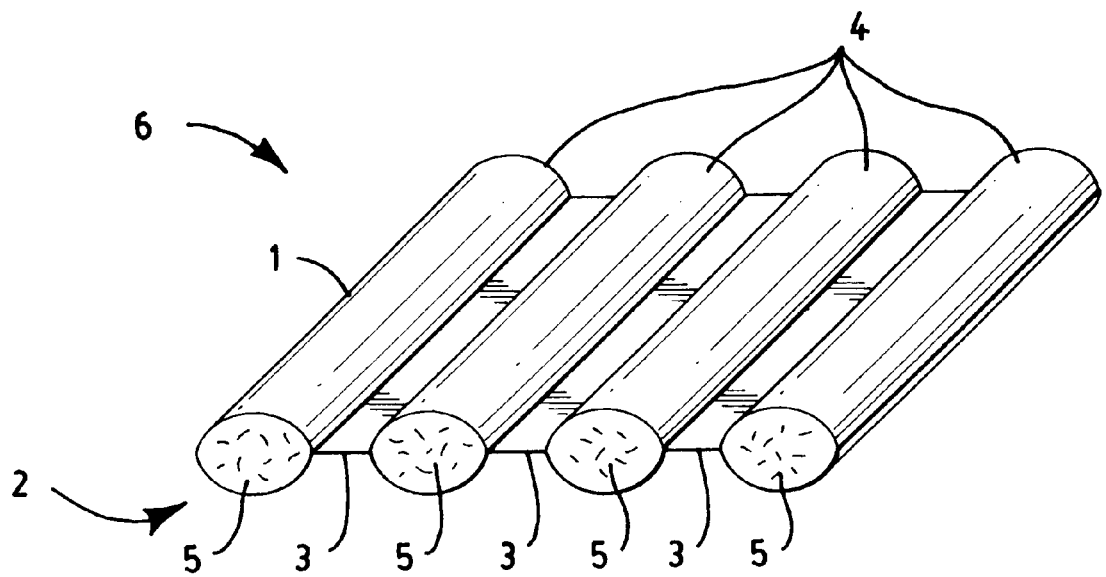
FIG. 1 is a drawing of a view of a stretchable absorbent showing a top sheet, a bottom sheet and beams of absorbent composition separated by bonded areas between the top and bottom sheets where the bonding is in one direction only.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than 90° are designated "nonwettable" or hydrophobic.

"Layer" when used in the singular can have the dual meaning of a single element or a plurality of elements.

"Liquid" means a nongaseous substance and/or material that flows and can assume the interior shape of a container into which it is poured or placed.

"Longitudinal" and "transverse" have their customary meanings. The longitudinal axis lies in the plane of the article and is generally parallel to a vertical plane that bisects a standing wearer into left and right body halves when the article is worn. The transverse axis lies in the plane of the article generally perpendicular to the longitudinal axis.

"Particles" refers to any geometric form such as, but not limited to flakes, granules, beads, powders, spherical grains or the like.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited onto a collecting surface.

As used herein, the term "machine direction" or MD means the length of a fabric in the direction in which it is produced. The term "cross machine direction" or CD means the width of fabric, i.e. a direction generally perpendicular to the MD.

As used herein, the term "coform" means a process in which at least one meltblown diehead is arranged near a chute through which other materials are added to the web while it is forming. Such other materials may be pulp, superabsorbent particles, cellulose or staple fibers, for example. Coform processes are shown in commonly assigned U.S. Pat. No. 4,818,464 to Lau and U.S. Pat. No. 4,100,324 to Anderson et al. Webs produced by the coform process are generally referred to as coform materials.

"Conjugate fibers" refers to fibers which have been formed from at least two polymer sources extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught, for example, in U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. No. 5,277,976 to Hogle et al. which describes fibers with unconventional shapes.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner.

"Bonded carded web" refers to webs that are made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

"Airlaying" is a well known process by which a fibrous nonwoven layer can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

As used herein, "ultrasonic bonding" means a process performed, for example, by passing the fabric between a sonic horn and anvil roll as illustrated in U.S. Pat. No. 4,374,888 to Bornslaeger.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

As used herein, through-air bonding means a process of bonding a fiber web in which air which is sufficiently hot to melt the polymers of which the fibers of the web are made is forced through the web. The air velocity is between 100 and 500 feet per minute and the dwell time may be as long as 6 seconds. The melting and resolidification of the polymer provides the bonding.

As used herein, the terms "elastic" and "elastomeric" when referring to a fiber, film or fabric mean a material which upon application of a biasing force, is stretchable to a stretched, biased length which is at least about 150 percent, or one and a half times, its relaxed, unstretched length, and which will recover at least 50 percent of its elongation upon release of the stretching, biasing force.

As used herein the term "recover" refers to a contraction of a stretched material upon termination of a biasing force following stretching of the material by application of the biasing force. For example, if a material having a relaxed, unbiased length of one (1) inch was elongated 50 percent by stretching to a length of one and one half (1.5) inches the material would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its elongation.

"Personal care product" means diapers, training pants, absorbent underpants, adult incontinence products, and feminine hygiene products.

DETAILED DESCRIPTION

The objects of this invention are achieved by an absorbent system which is stretchable and includes valleys which may retain liquid for absorption and direct liquid in various directions. The stretchable absorbent material of this invention can perform surge, distribution and containment functions to various degrees and the provision of these functions in only one material can result in a savings in material and manufacturing costs.

The stretchable absorbent material of this invention includes a top and bottom layer comprised of a material including films, nonwoven fabrics, tissues or a combination thereof. The preferred materials for the top and bottoms layers may be made by the spunbond, meltblown and wetlaid processes. The top layer refers to the layer toward the wearer and the bottom layer is the layer away from the wearer. The top and bottoms layers may independently be stretchable or elastic though neither must be. The top layer must be permeable to liquid though the bottom layer need not be permeable, so, if a film is used as the top sheet it must be apertured, perforated, or in some other way made liquid permeable.

Turning now to FIG. 1, one may see a top sheet 1 and bottom sheet 2 bonded at spaced apart rows 3 between which are "beams" 4 of an absorbent composition 5 in order to produce a stretchable absorbent material 6. For purposes of discussion assume that the beams 4 run in the machine direction, making the cross-machine direction perpendicular to the direction of the beams 4.

Figure 2:
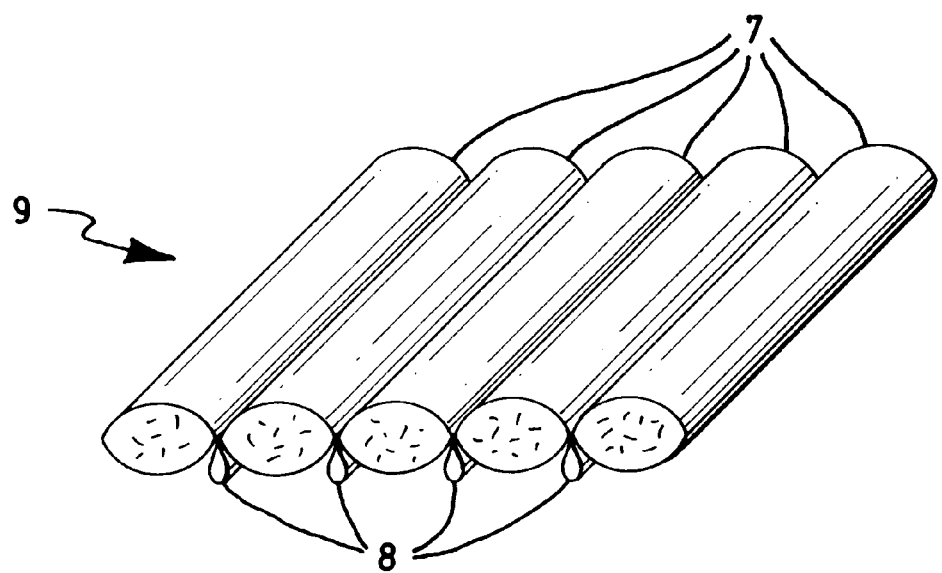
FIG. 2 is a drawing of a view of a stretchable absorbent showing a top sheet, a bottom sheet and beams of absorbent composition separated by bonded areas between the top and bottom sheets where the rows are gathered together or "festooned" out between the beams.

If the top sheet and bottom sheet are non-stretchable, stretchability will be provided to the absorbent material by the compression of the absorbent composition in the beams when a stretching force is applied to the absorbent material in the cross-machine direction. Recovery may also be provided depending on the recovery characteristics of the absorbent composition chosen. Alternatively, the absorbent material may be made stretchable by arranging it in a manner such that the rows are gathered together or "festooned" out between the beams as shown in FIG. 2. The beams 7 in FIG. 2 are brought closer together, causing the material from which the rows 8 are made to gather. When a stretching force is applied in a direction perpendicular to the beams 7, the material in the rows 8 will become "unfestooned" or less gathered, so providing stretch to the absorbent material 9.

If the top sheet and bottom sheet are stretchable, more stretchability will be provided to the absorbent material since the bond rows will also stretch. Lastly, if the top sheet and bottom sheet are elastic, stretchability will, of course, be provided, but recovery properties will also be quite strong as the elastic nature of the sheets pulls the absorbent material back towards its original dimensions upon the release of the stretching force. The recovery force may be regulated as desired by the selection of the type and amount of elastic used to produce the sheets and also by the choice of whether both sheets or merely one sheet is elastic.

There may be an advantage in certain applications in having the bottom sheet be liquid permeable, such as, for example, in a diaper with a liquid impermeable outer cover. In this instance, liquid can penetrate the absorbent material and a portion can be absorbed by the absorbent composition therein, and a further portion of the liquid can continue through the absorbent material and exit the bottom sheet. Liquid leaving the bottom sheet would be free to move within the diaper in the space between the bottom sheet and any subjacent layers, be contained by the impermeable outercover, and reenter the absorbent material at another location, preferably where the liquid loading on the absorbent composition is not as great as the point at which the liquid left the bottom sheet. In such a way, the space between the absorbent material and the subjacent layers, e.g. the outercover, may fulfill the distribution functionality so desired in more advanced diaper designs. Particular distribution materials may be designed and provided to take advantage of a permeable bottom sheet by absorbing liquid exiting the bottom sheet, moving the liquid, and then releasing the liquid at preferred locations.

The design of this invention provides a myriad of benefits when incorporated into a personal care product such as a diaper. These benefits include conformability, liquid distribution, surface dryness, BM (feces) management, breathability or air circulation, and reduced wet bulk, which will be addressed below in order.

The conformability of a personal care product refers to the fit of the product on the wearer, particularly when the wearer moves. A highly conformable product not only feels better to the wearer since it does not bind or pull, but reduces the likelihood of leakage from the product. The stretchable and elastic embodiments of the invention help provide a good degree of conformability to a personal care product into which they may be incorporated.

Clearly, the rows and beams in the absorbent material form valleys and peaks. Liquid may move through these valleys, providing distribution functionality, and may also be held, providing surge functionality. As the absorbent composition within the absorbent material absorbs liquid and swells, the valleys should become deeper and more pronounced, allowing even greater liquid flow. Further enhancement of the liquid distribution may be achieved by the chemical treatment of the top and/or bottom sheets in the valleys with surfactants to increase wettability. Inherently wettable fibers may also be used in the valleys to increase wettability as well. The wettability of the valleys, particularly in fibrous embodiments, will serve to increase wicking along the valley floor and transfer liquid to regions away from the target area. Since superabsorbents tend to lock up liquid at the insult point, others have tried to remove the superabsorbent from the target area entirely, though this may increase the chance of leakage. The design of the present invention does not entirely remove superabsorbent from the target area but provides an opportunity to move some of the liquid insult along the valley floor before it is completely absorbed. Varying the amount or absorption speed of the superabsorbent in the beams is yet another method of controlling the amount of liquid absorbed versus the amount of liquid available for movement.

Liquid distribution can also be improved by the physical arrangement of the rows and beams in, for example, a diaper. If the rows and beams are run in a longitudinal direction, liquid movement toward the leg openings is impeded by multiple peaks and valleys (in embodiments so provided) between the target area and the leg opening, with the peaks between each valley acting as a liquid barrier or dam.

Figure 3:
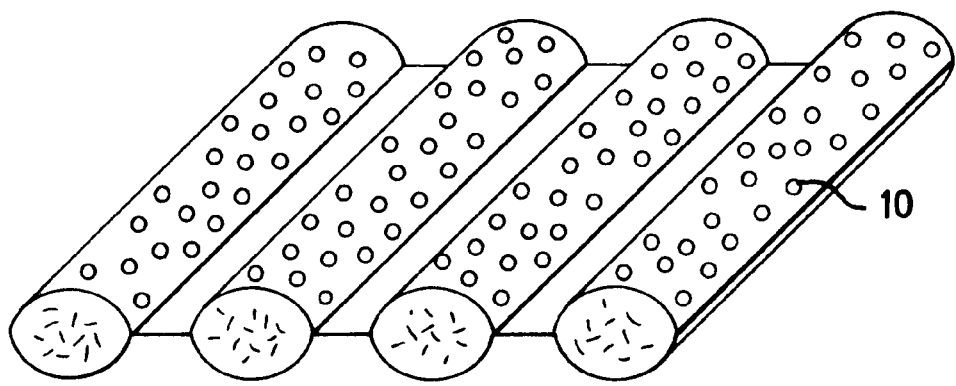
FIG. 3 is a drawing of a view of a stretchable absorbent showing a top sheet, a bottom sheet and beams of absorbent composition separated by bonded areas between the top and bottom sheets where the top sheet is provided with holes.

It is highly desirable to keep the surface of a personal care product dry for the comfort of the wearer and a saturated wet absorbent is a major source of surface wetness. Promoting surface dryness may be accomplished by the invention by geometry and chemical treatment. The geometric arrangement of the rows and beams is such that the valleys will not normally be in contact with the skin of the wearer even if the absorbent material is placed directly against the skin, thus minimizing the total area of skin contact. Chemical treatment can be used to provide a top sheet that is hydrophobic or non-wettable. A hydrophobic top sheet will not allow liquid to remain on the peaks, so maintaining the area in contact with the skin in a dry condition. A completely hydrophobic top sheet, however, would require some manner of allowing liquid to pass through it to the absorbent in the beams, such as perforations, apertures, etc., as shown in FIG. 3 which illustrates such holes 10. Alternatively, only a portion of the top sheet, e.g., the peaks, could be made hydrophobic, (and optionally treating the valleys to make them hydrophilic) thus allowing part of the top sheet to remain liquid permeable and yet maintain the peak area which is in skin contact in a dry state.

The valleys produced by the rows and beams can also function as BM containment devices, i.e. to contain solid exudates from the wearer and prevent them from escaping from a personal care product, like a diaper, into which the absorbent material is incorporated. The space provided by the valleys can greatly reduce the amount of BM that contacts the wearer. A chemical treatment of the top sheet may also be used to enhance BM movement into the valleys by making the top sheet more slippery or slick, by, for example, using a silicone. In order for the valleys to function as BM containment, of course, would require that no other layer, such as a liner, which would prevent BM from reaching the absorbent material, be placed between the absorbent material and the wearer's skin. It is also desirable for BM containment, that the valleys be maintained after receiving BM. The maintenance of the valleys may be accomplished by providing collapse or compression resistant beams by incorporating compression resistant materials like foams into the beams. The foams may be chopped into small pieces and mixed with the other beam contents during production.

Breathability is a major focus in the development of personal care products because of the concern with rashes and the discomfort they cause the wearer. The valleys created by the row and beam design of the invention can function to improve air circulation or breathability within a personal care product and so aid in maintaining skin wellness. The geometry of the invention can provide direct, unimpeded air flow from the outside of a personal care product via the valley regions. Air may also pass through the top and bottom sheets (when the bottom sheet is not impermeable).

The rows of the absorbent material may range in size from about 2 mm to about 50 mm in width. The beams of the absorbent material may range in size from about 5 mm to about 100 mm in width. A pattern such as those shown in U.S. patent application Ser. No. 08/622,493, for which the issue fee has been paid, may also be used. Optimization of the row and beam sizes may be accomplished in order to produce valleys giving the most desired properties for a given application.

In another aspect of this invention, it is also possible to choose bonding strengths in creating the rows, such that as the absorbent composition absorbs liquid and swells, the bonds detach and allow the absorbent composition to flow into and fill the space between the top sheet and bottom sheet where the bond had been. A bond strength lower than the burst strength of either the top sheet or bottom sheet would help ensure that neither sheet would burst. If either sheet were to burst it would allow absorbent composition to escape within a personal care product containing the absorbent article 6, which is undesirable. In this design, the absorbent composition could be allowed to float freely, i.e. be unattached, within the beams, so that it would be free to move into the space opened by the separation of the row bonds.

Traditional absorbent systems for personal care products may be generalized as having the functions of surge control and containment (retention) or SC. The absorbent material of this invention may be used in conjunction with the other functional materials in a personal care product. Other functional layers also include distribution layers and, for example, liners and backsheets.

The surge control function is to quickly accept the incoming insult and either absorb, hold, channel or otherwise manage the liquid so that it does not leak outside the article. A surge layer may also be referred to as an intake layer, transfer layer, transport layer and the like and is most typically interposed between and in intimate, liquid communicating contact with the bodyside liner and another layer such as a retention layer to which it may be attached.

A material providing surge functionality must typically be capable of handling an incoming insult of between about 60 and 100 cc at a velocity of from about 5 to 20 cc/sec, for infants, for example. Surge control is typically provided by a fluff pulp in an absorbent product or by a high permeability nonwoven layer. For example, the surge layer may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The surge layer also can be a bonded carded web or an airlaid web composed of natural and/or synthetic fibers. The bonded carded web may, for example, be a powder bonded carded web, an infrared bonded carded web, or a through-air bonded carded web. The carded webs can optionally include a mixture or blend of different fibers, and the fiber lengths within a selected web may range from about 3 mm to about 60 mm. One exemplary surge material may be found in coassigned U.S. patent application Ser. No. 08/755,514, which presents a surge material which is a wettable web of fibers of at most 30 microns in diameter where the web has a permeability between about 250 and 1500 Darcys, a capillary tension between about 1.5 and 5 cm, and which maintains that permeability and capillary tension over the life of the web. It is preferred that the web have a density between about 0.02 g/cc to about 0.07 g/cc. Another exemplary surge material may be found in coassigned U.S. patent application Ser. No. 08/754,417. Traditional fibrous surges described above function by providing interstitial areas in which liquid may be held.

A surge layer may be used in conjunction with the absorbent material of this invention to hold and spread liquid over a larger area of the absorbent material. Such a traditional surge would compliment the inventive absorbent material by providing more time for absorption by holding a portion of the liquid insult in the surge's interstitial voids prior to contact with the absorbent material of this invention. Under pressure exerted by the wearer, the interstitial liquid in the surge layer can be released to the valleys of the absorbent material for immediate retention or distribution to other regions of the article.

The containment or retention function is to absorb the insult quickly and efficiently. A material providing retention functionality should be capable of pulling liquid from the distribution layer and absorbing liquid without significant "gel blocking" or blocking of penetration of liquid further into the absorbent by the expansion of the outer layers of absorbent. Retention is often provided by absorbent compositions such as those containing high rate superabsorbent polymers such as blends of polyacrylate superabsorbent and fluff. These materials rapidly absorb and hold liquid. Examples of suitable superabsorbents include Favor 870 which is commercially available from the Stockhausen Company of Greensboro, N.C. 27406 and which is a highly crosslinked surface superabsorbent, AFA 94-21-5, which is a 850 to 1400 micron suspension polymerized polyacrylate particle from The Dow Chemical Company of Midland, Mich., 48674, and XL AFA-126-15 polyacrylate bead, also from The Dow Chemical Company. Fluff examples include CR 1654 pulp which is commercially available from the Kimberly-Clark Corporation of Dallas, Tex. and is a southern softwood pulp, CR-2054 pulp, also from Kimberly-Clark Corporation, and high bulk additive formaldehyde free (HBAFF) pulp which is available from the Weyerhaeuser Corporation of Tacoma, Wash., and is a which is a crosslinked southern softwood pulp fiber with enhanced wet modulus. HBAFF has a chemical treatment which sets in a curl and twist, in addition to imparting added dry and wet stiffness and resilience to the fiber. A binder may be present in containment material to mechanically stabilize the absorbent structure. An exemplary binder is from Danaklon a/s, located at Engdraget 22, KD-6800 Varde, Denmark, and is 2 denier conjugate polyethylene/polypropylene (PE/PP) sheath/core conjugate fibers cut into 6 mm lengths. Another exemplary binder is a liquid binder such as Kymene® 557LX binder available from Hercules Inc. of Wilmington, Del. Superabsorbents may also be in the form of fibers and foams.

In addition to the surge control and containment functions in traditional absorbent systems, recent work has introduced another function which may be a separate layer interposed between the S and C layers or may be incorporated into existing materials. This new function is a distribution function, producing a system with surge control, distribution and containment or "SDC".

The distribution function is to move fluid from the point of initial deposition to where storage is desired. Distribution should preferably take place at an acceptable speed such that the target insult area, generally the crotch area, is ready for the next insult. The time between insults can range from just a few minutes to hours, generally depending on the age of the wearer.

Materials from which the distribution layer may be made include woven fabrics and nonwoven webs. For example, a distribution layer may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The distribution layer also can be a bonded carded web, an airlaid web or a wetlaid pulp structure composed of natural and/or synthetic fibers, or a combination thereof.

Absorbent products such as, for example, diapers, generally also have a liner which goes against the wearer, a backsheet which is the most exterior layer, and may also contain other layers.

The liner is sometimes referred to as a bodyside liner or topsheet and is adjacent the surge material. In the thickness direction of the article, the liner material is the layer against the wearer's skin and so the first layer in contact with liquid or other exudate from the wearer. The liner further serves to isolate the wearer's skin from the liquids held in an absorbent structure and should be compliant, soft feeling and non-irritating.

Various materials can be used in forming the bodyside liner of the present invention, including apertured plastic films, woven fabrics, nonwoven webs, porous foams, reticulated foams and the like. Nonwoven materials have been found particularly suitable for use in forming the bodyside liner, including spunbond or meltblown webs of polyolefin filaments, or bonded carded webs of natural polymers (for example, rayon or cotton fibers) and/or synthetic polymers (for example, polypropylene or polyester) fibers. For example, the bodyside liner can be a nonwoven spunbond web of synthetic polypropylene filaments. The nonwoven web can have a basis weight, for example, ranging from about 10.0 grams per square meter (gsm) to about 68.0 gsm, and more particularly from about 14.0 gsm to about 42.0 gsm, a bulk or thickness ranging from about 0.13 millimeter (mm) to about 1.0 mm, and more particularly from about 0.18 mm to about 0.55 mm, and a density between about 0.025 grams per cubic centimeter (g/cc) and about 0.12 g/cc, and more particularly between about 0.068 g/cc and about 0.083 g/cc. Additionally, the permeability of such a nonwoven web can be from about 150 Darcy to about 5000 Darcy. The nonwoven web can be surface treated with a selected amount of surfactant, such as about 0.28% Triton X-102 surfactant, or otherwise processed to impart the desired level of wettability and hydrophilicity. If a surfactant is used, it can be an internal additive or applied to the web by any conventional means, such as spraying, printing, dipping, brush coating and the like.

The backsheet is sometimes referred to as the outer cover and is the farthest layer from the wearer. The outer cover is typically formed of a thin thermoplastic film, such as polyethylene film, which is substantially impermeable to liquid. The outer cover functions to prevent body exudates contained in an absorbent structure from wetting or soiling the wearer's clothing, bedding, or other materials contacting the diaper. The outer cover may be, for example, a polyethylene film having an initial thickness of from about 0.5 mil (0.012 millimeter) to about 5.0 mil (0.12 millimeter). The polymer film outer cover may be embossed and/or matte finished to provide a more aesthetically pleasing appearance. Other alternative constructions for outer cover include woven or nonwoven fibrous webs that have been constructed or treated to impart the desired level of liquid impermeability, or laminates formed of a woven or nonwoven fabric and thermoplastic film. The outer cover may optionally be composed of a vapor or gas permeable, microporous "breathable" material, that is permeable to vapors or gas yet substantially impermeable to liquid. Breathability can be imparted to polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability. Some embodiments of backings may also serve the function of a mating member for mechanical fasteners.

As previously noted, the top sheet and bottom sheet may be made from various materials including nonwoven fabrics, films, tissues and combinations thereof. The fabrics and films may be made by conventionally known means of various thermoplastic polymers. For example, polyolefins such as Dow Chemical's ASPUN® 6811A linear low density polyethylene, 2553 LLDPE and 25355 and 12350 high density polyethylene are such suitable polymers. The polyethylenes have melt flow rates, respectively, of about 26, 40, 25 and 12. Suitable polypropylenes include Exxon Chemical Company's Escorene® PD 3445 polypropylene and Montell Chemical Co.'s PF-304. Many other polyolefins are commercially available.

Elastomeric thermoplastic polymers useful in the practice of this invention may be those made from block copolymers such as polyurethanes, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene) and the like.

Useful elastomeric resins include block copolymers having the general formula A-B-A' or A-B, where A and A' are each a thermoplastic polymer endblock which contains a styrenic moiety such as a poly (vinyl arene) and where B is an elastomeric polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. In this regard, the radial block copolymers may be designated $(A-B)_m-X$, wherein X is a polyfunctional atom or molecule and in which each $(A-B)_m-$ radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer", and particularly "A-B-A'" and "A-B" block copolymer, is intended to embrace all block copolymers having such rubbery blocks and thermoplastic blocks as discussed above, which can be extruded (e.g., by meltblowing), and without limitation as to the number of blocks. The elastomeric nonwoven web may be formed from, for example, elastomeric (polystyrene/poly(ethylene-butylene)/polystyrene) block copolymers. Commercial examples of such elastomeric copolymers are, for example, those known as KRATON® materials which are available from Shell Chemical Company of Houston, Tex. KRATON® block copolymers are available in several different formulations, a number of which are identified in U.S. Pat. Nos. 4,663,220, 4,323,534, 4,834,738, 5,093,422 and 5,304,599, hereby incorporated by reference, each in its entirety.

Polymers composed of an elastomeric A-B-A-B tetrablock copolymer may also be used in the practice of this invention. Such polymers are discussed in U.S. Pat. No. 5,332,613 to Taylor et al. In such polymers, A is a thermoplastic polymer block and B is an isoprene monomer unit hydrogenated to substantially a poly(ethylene-propylene) monomer unit. An example of such a tetrablock copolymer is a styrene-poly(ethylene-propylene)-styrene-poly(ethylene-propylene) or SEPSEP elastomeric block copolymer available from the Shell Chemical Company of Houston, Tex. under the trade designation KRATON® G-1657.

Other exemplary elastomeric materials which may be used include polyurethane elastomeric materials such as, for example, those available under the trademark ESTANE® from B. F. Goodrich & Co. or MORTHANE® from Morton Thiokol Corp., polyester elastomeric materials such as, for example, those available under the trade designation HYTREL® from E. I. duPont De Nemours & Company, and those known as ARNITEL®, formerly available from Akzo Plastics of Arnhem, Holland and now available from DSM of Sittard, Holland.

Another suitable material is a polyester block amide copolymer having the formula:

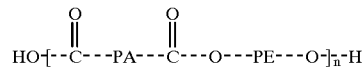

where n is a positive integer, PA represents a polyamide polymer segment and PE represents a polyether polymer segment. In particular, the polyether block amide copolymer has a melting point of from about 150° C. to about 170° C., as measured in accordance with ASTM D-789; a melt index of from about 6 grams per 10 minutes to about 25 grams per 10 minutes, as measured in accordance with ASTM D-1238, condition Q (235 C/1 Kg load); a modulus of elasticity in flexure of from about 20 Mpa to about 200 Mpa, as measured in accordance with ASTM D-790; a tensile strength at break of from about 29 Mpa to about 33 Mpa as measured in accordance with ASTM D-638 and an ultimate elongation at break of from about 500 percent to about 700 percent as measured by ASTM D-638. A particular embodiment of the polyether block amide copolymer has a melting point of about 152° C. as measured in accordance with ASTM D-789; a melt index of about 7 grams per 10 minutes, as measured in accordance with ASTM D-1238, condition Q (235 C/1 Kg load); a modulus of elasticity in flexure of about 29.50 Mpa, as measured in accordance with ASTM D-790; a tensile strength at break of about 29 Mpa, a measured in accordance with ASTM D-639; and an elongation at break of about 650 percent as measured in accordance with ASTM D-638. Such materials are available in various grades under the trade designation PEBAX® from ELF Atochem Inc. of Glen Rock, N.J. Examples of the use of such polymers may be found in U.S. Pat. Nos. 4,724,184, 4,820,572 and 4,923,742 hereby incorporated by reference in their entirety, to Killian et al. and assigned to the same assignee as this invention.

Elastomeric polymers also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

The thermoplastic copolyester elastomers include copolyetheresters having the general formula:

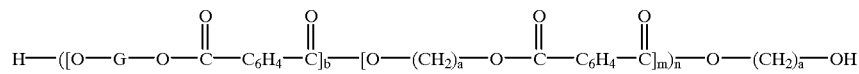

where "G" is selected from the group consisting of poly(oxyethylene)-alpha,omega-diol, poly(oxypropylene)-alpha, omega-diol, poly(oxytetramethylene)-alpha,omega-diol and "a" and "b" are positive integers including 2, 4 and 6, "m" and "n" are positive integers including 1–20. Such materials generally have an elongation at break of from about 600 percent to 750 percent when measured in accordance with ASTM D-638 and a melt point of from about 350° F. to about 400° F. (176 to 205° C.) when measured in accordance with ASTM D-2117.

Commercial examples of such copolyester materials are, for example, those known as ARNITEL®, formerly available from Akzo Plastics of Arnhem, Holland and now available from DSM of Sittard, Holland, or those known as HYTREL® which are available from E. I. duPont de Nemours of Wilmington, Del. Formation of an elastomeric nonwoven web from polyester elastomeric materials is disclosed in, for example, U.S. Pat. No. 4,741,949 to Morman et al. and U.S. Pat. No. 4,707,398 to Boggs, hereby incorporated by reference.

Suitable elastomeric polymers also include a relatively new class of polymers which has excellent barrier, breathability and elasticity. The new class of polymers have a narrow polydispersity number, e.g.; Mw/Mn is 4 or less and may be produced according to the metallocene process.

The metallocene process generally uses a catalyst which is activated, i.e. ionized, by a co-catalyst. An exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow.

The metallocene process is the subject of a number of patents, for example, U.S. Pat. No. 4,542,199 to Kaminsky et al., U.S. Pat. No. 5,189,192 to LaPointe et al., U.S. Pat. No. 5,352,749 to Exxon Chemical Patents, Inc., U.S. Pat. Nos. 5,278,272 and 5,272,236, both to Lai et al., U.S. Pat. No. 5,204,429, and U.S. Pat. No. 5,349,100.

Polymers produced using metallocene catalysts have the unique advantage of having a very narrow molecular weight range. Polydispersity numbers (Mw/Mn) of below 4 and as even below 2 are possible for metallocene produced polymers. These polymers also have a controlled short chain branching distribution when compared to otherwise similar Ziegler-Natta produced type polymers.

It is also possible using a metallocene catalyst system to control the isotacticity of the polymer quite closely when stereo selective metallocene catalysts are employed. In fact, polymers have been produced having an isotacticity of in excess of 99 percent. It is also possible to produce highly syndiotactic polypropylene using this system.

Controlling the isotacticity of a polymer can also result in the production of a polymer which contains blocks of isotactic and blocks of atactic material alternating over the length of the polymer chain. This construction results in an elastic polymer by virtue of the atactic portion. Such polymer synthesis is discussed in the journal *Science*, vol. 267, Jan. 13, 1995) at p. 191 in an article by K. B. Wagner. Wagner, in discussing the work of Coates and Waymouth, explains that the catalyst oscillates between the stereochemical forms resulting in a polymer chain having running lengths of isotactic sterocenters connected to running lengths of atactic centers. Isotactic dominance is reduced producing elasticity. Geoffrey W. Coates and Robert M. Waymouth, in an article entitled "Oscillating Stereocontrol: A Strategy for the Synthesis of Thermoplastic Elastomeric Polypropylene" at page 217 in the same issue, discuss their work in which they used metallocene bis(2-phenylindenyl)-zirconium dichloride in the presence of methylaluminoxane (MAO), and, by varying the pressure and temperature in the reactor, oscillate the polymer form between isotactic and atactic.

Metallocene polymers are available from Exxon Chemical Company under the trade name ACHIEVE® for polypropylene based polymers and EXACT® and EXCEED® for polyethylene based polymers. Dow Chemical Company of Midland, Mich. has polymers commercially available under the name ENGAGE®. These materials are believed to be produced using non-stereo selective metallocene catalysts. Exxon generally refers to their metallocene catalyst technology as "single site" catalysts while Dow refers to theirs as "constrained geometry" catalysts under the name INSIGHT® to distinguish them from traditional Ziegler-Natta catalysts which have multiple reaction sites. In the practice of the instant invention, elastic polyolefins like polypropylene and polyethylene are preferred, most especially elastic polypropylene.

Other suitable polymers for the film and/or nonwoven layers are available commercially under the trade designation "Catalloy" from the Montell Chemical Company of Wilmington, Del., and polypropylene. Specific commercial examples are Catalloy KS-084P and Catalloy KS-057P. Catalloy polymers are disclosed in European Patent Application EP 0444671 A3 (based on Application number 91103014.6), European Patent Application EP 0472946 A2 (based on Application number 91112955.9), European Patent Application EP 0400333 A2 (based on Application number 90108051.5), U.S. Pat. No. 5,302,454 and U.S. Pat. No. 5,368,927.

Processing aids may be added to the elastomeric polymer as well. A polyolefin, for example, may be blended with the elastomeric polymer (e.g., the elastomeric block copolymer) to improve the processability of the composition. The polyolefin must be one which, when so blended and subjected to an appropriate combination of elevated pressure and elevated temperature conditions, is extrudable, in blended form, with the elastomeric polymer. Useful blending polyolefin materials include, for example, polyethylene, polypropylene and polybutene, including ethylene copolymers, propylene copolymers and butene copolymers. A particularly useful polyethylene may be obtained from the U.S.I. Chemical Company under the trade designation Petrothene NA 601 (also referred to herein as PE NA 601 or polyethylene NA 601). Two or more of the polyolefins may be utilized. Extrudable blends of elastomeric polymers and polyolefins are disclosed in, for example, U.S. Pat. No. 4,663,220.

The absorbent materials of this invention may also have topical treatments applied to them for more specialized functions. Such topical treatments and their methods of application are known in the art and include, for example, alcohol repellence treatments, anti-static treatments and the like, applied by spraying, dipping, etc. An example of such a topical treatment is the application of Zelec® antistat, available from E. I. duPont, Wilmington, Del.

Materials of construction for the absorbent composition of the stretchable absorbent material of this invention have been discussed previously. The absorbent composition may include 20 to 100 weight percent of superabsorbent, from 80 to 0 weight percent pulp and optionally from a positive amount to about 10 weight percent of a binder. The absorbent composition may be made according to known processes, such as by the coform process and may incorporate foam to increase compression resistance as discussed above.

The stretchable absorbent material of this invention may be made, for example, by depositing a film and/or nonwoven onto a moving conveyor belt or "forming wire", depositing the desired absorbent composition in rows onto the film and/or nonwoven, depositing a second layer of film and/or nonwoven over the absorbent composition, and then bonding the layers together in rows between the absorbent composition. Bonding may be accomplished by means known in the art such as thermally, chemically, ultrasonically, etc. Alternatively, the stretchable absorbent material may be made by providing a previously produced film and/or nonwoven web, depositing the absorbent composition in rows, and then either depositing a newly formed film and/or nonwoven layer or providing a previously produced layer, and then bonding the layers together. In either case, the absorbent composition may be deposited in machine directional or cross-machine directional rows, depending on the direction of stretch desired, since, as previously taught, the material will stretch in a direction perpendicular to the direction of the rows and beams.

Yet another method of making the absorbent material of this invention is to provide a bonded carded web of staple fibers, placing multiple yarns of tow of fibrous superabsorbent onto the bonded carded web, providing a second bonded carded web on top of the tow and first bonded carded web, and ultrasonically bonding the two bonded carded webs together at spaced apart rows between the fibrous superabsorbent tows. Such an embodiment was produced using 146 gsm of a fibrous superabsorbent known as Fibersorb®, which is a 100 percent fibrous superabsorbent formerly available from the Arco Chemical Company of Newtown Square, Pa., between two layers of 50 gsm through air bonded carded web material made from 60 weight percent 3 denier bicomponent binder fiber from BASF Corporation, Enka, N.C., and 40 weight percent 6 denier polyester (PET) fiber from Hoechst Celanese of Charlotte, N.C. Fibrous superabsorbents are also available as Oasis® superabsorbent from Technical Absorbents of Grimsby, UK and Fiberdri® superabsorbents from Camelot Superabsorbents Inc., Charlotte, N.C.

In yet another embodiment, the absorbent composition may be a mixture of meltblown elastomeric fibers, optionally treated for wettability, and superabsorbent. The meltblown fibers provide liquid storage space in the interstitial areas and also act as a binder for the superabsorbent particles. The meltblown fibers may be present in an amount up to 50 weight percent.

Another embodiment produced by the inventors used Lycra® elastic threads laminated between two layers of 20 gsm spunbond polypropylene fabric for the top and bottom layers. The Lycra® threads were spaced about 5 mm apart and attached to the two spunbond layers using a hot melt adhesive. Thermal bonding was used to produce the absorbent material by bonding two layers of the spunbond/Lycra® thread/spunbond laminate together with row widths of about 4 mm spaced about 35 mm apart using a Vertrod Thermal Impulse Heat Sealing Machine (model 20P) from the Vertrod Corporation of Toccoa, Ga. The heat sealer had a dwell time of 1.5 and a heat rate of 2.5 on a scale of 1–10. The spunbond and Lycra® thread laminate stretched 160 percent and recovered 100 percent. An absorbent composition was placed between the rows prior to bonding and comprised about 37 weight percent Favor® 870 superabsorbent, and about 63 weight percent CR-1654 fluff pulp. The absorbent material so produced had a basis weight of about 550 gsm.

In another embodiment, an elastic film (code X-MAX 264.0) from CT Films Corporation was used as the top and bottom layers. This film stretches in both MD and CD directions. The bonds were about 3 mm in width and the unbonded area about 50 mm wide. The superabsorbent used was a composite having a width of about 30 mm which was not attached to either the top or bottom layer, i.e. it was contained or "floated" in a pocket between the bonds. As a result, the absorbent material could stretch in a direction parallel with the beams, not just perpendicular to it, even though the bond rows were parallel to the beams. Thus, this material had both CD and MD stretch properties when the stretching force is applied to the top and bottom sheets. It is interesting to note that in this embodiment, even though the bond row was only about 3 mm in width, the distance between the superabsorbent beams was substantially greater since much of the pocket between the rows remained empty by virtue of the difference between the absorbent width (30 mm) and the distance between bonds (50 mm).

Figure 4:
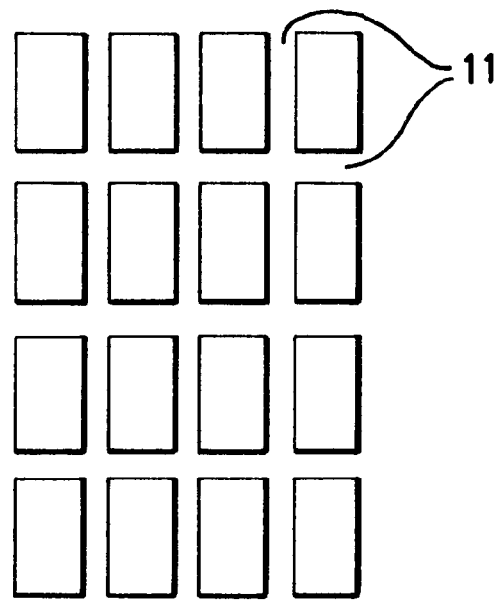
FIG. 4 is a plan view of a stretchable absorbent showing bonding in both the machine direction (MD) and cross-machine direction (CD) which provides CD and MD stretchability.

In another manner of producing a stretchable absorbent material which stretches in both the MD and CD, the absorbent composition should be deposited in a discontinuous manner so that bonds 11 may be provided in both the MD and CD directions as shown in FIG. 4.

The stretchable absorbent material of this invention may be incorporated into a personal care product like a diaper with the rows and beams running longitudinally or transversely, depending upon the desired movement of liquid. The longitudinal direction is preferred in a diaper as it is usually desired to move liquid away from the target zone to the extreme front or back.

As can be seen from the above description, there is herein provided an absorbent article wherein some of an insult may be moved away from the target zone and wherein the absorbent is stretchable. This provides a great advance in absorbent technology and personal care product design.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. An elastic absorbent material for personal care products comprising an elastic liquid permeable top sheet, an elastic bottom sheet, and beams of an absorbent composition between said top and bottom sheets whereby said beams are spaced apart by rows of bonds therebetween which bond together the top and bottom sheets, wherein said bonds break to accommodate the expansion of said absorbent composition upon exposure to liquids and wherein the top and bottom sheets are elastic such that when said top and bottom sheets are stretched to a length that is at least about 150 percent a relaxed, unstretched length by a biasing force, said top and bottom sheets will recover at least 50 percent elongation upon release of said biasing force.

2. The elastic absorbent material of claim 1 wherein said bottom sheet is liquid permeable.

3. The elastic absorbent material of claim 1 wherein said bottom sheet is liquid impermeable.

4. The elastic absorbent material of claim 1 wherein said absorbent composition comprises a mixture of superabsorbent particles and wood pulp fluff.

5. The elastic absorbent material of claim 1 wherein said rows are between about 2 and about 50 mm in width and said beams are between about 5 and 100 mm in width.

6. An absorbent material according to claim 1 having a superabsorbent selected from the group consisting of fibers, particles, foams and combination thereof.

7. An absorbent material according to claim 1 whereby air flows through said material in the valleys.

8. A personal care product selected from the group consisting of diapers, training pants, absorbent underpants, adult incontinence products and feminine hygiene products comprising the material of claim 1.

9. The product of claim 8 wherein said personal care product is a feminine hygiene product.

10. The product of claim 8 wherein said personal care product is an adult incontinence product.

11. The product of claim 8 wherein said personal care product is a diaper.

\* \* \* \* \*